(12) United States Patent
Faulconbridge et al.

(10) Patent No.: US 10,512,855 B2
(45) Date of Patent: Dec. 24, 2019

(54) METHOD FOR EXTRACTING OIL FROM A WATER AND SOLIDS COMPOSITION, METHOD FOR THE PRODUCTION OF ETHANOL, AND ETHANOL PRODUCTION FACILITY

(71) Applicant: KFI Intellectual Properties L.L.C., St. Paul, MN (US)

(72) Inventors: James Faulconbridge, Maplewood, MN (US); Robert Wills, Brooklyn Park, MN (US)

(73) Assignee: KFI Intellectual Properties L.L.C., St. Paul, MN (US)

( * ) Notice: Subject to any disclaimer, the term of this patent is extended or adjusted under 35 U.S.C. 154(b) by 562 days.

(21) Appl. No.: 15/041,053

(22) Filed: Feb. 11, 2016

(65) Prior Publication Data
US 2016/0303491 A1    Oct. 20, 2016

Related U.S. Application Data

(62) Division of application No. 14/011,342, filed on Aug. 27, 2013, now Pat. No. 9,260,676, which is a division
(Continued)

(51) Int. Cl.
*B01D 11/04*      (2006.01)
*C11B 1/10*       (2006.01)
(Continued)

(52) U.S. Cl.
CPC .......... *B01D 11/0426* (2013.01); *B01D 3/002* (2013.01); *B01D 3/143* (2013.01);
(Continued)

(58) Field of Classification Search
CPC ....... B01D 11/0426; B01D 3/002; C11B 1/10; C11B 1/102
(Continued)

(56) References Cited

U.S. PATENT DOCUMENTS 2,279,408 A    4/1942 McDonald
3,869,438 A    3/1975 Finley et al.
(Continued)

FOREIGN PATENT DOCUMENTS

EP    0 969 079    1/2000
GB    1 385 600    2/1975
(Continued)

OTHER PUBLICATIONS

Campos et al., "Production of Acetone Butanol Ethanol from Degermed Corn Using *Clostridium beijerinckii* BA101", Applied Biochemistry and Biotechnology, vol. 98-100, pp. 553-561, Copyright 2002.
(Continued)

*Primary Examiner* — Deborah D Carr
(74) *Attorney, Agent, or Firm* — Merchant & Gould P.C.

(57) ABSTRACT

The present disclosure includes a method for processing a beer stream for the recovery of oil. The method include a step of extracting oil from a beer stream into an organic phase comprising an organic solvent to provide in the organic phase at least a portion of the oil. In general, a beer stream refers to a composition containing alcohol, water, oil, and particulates, and can be a result of a fermentation process. When the beer stream is a beer stream from a fermentation process, it can be referred to as a fermentation broth even if it is no longer being subjected to fermentation. The beer stream can contain other components commonly found in a stream coming off a fermentation process such as, for example, glycerol and acetic acid. A method for producing ethanol, and an ethanol production facility are provided.

8 Claims, 2 Drawing Sheets

Related U.S. Application Data of application No. 12/215,913, filed on Jun. 30, 2008, now Pat. No. 8,518,673.

(60) Provisional application No. 60/947,120, filed on Jun. 29, 2007.

(51) Int. Cl.
| | |
|---|---|
| *C12P 7/06* | (2006.01) |
| *C11B 3/00* | (2006.01) |
| *B01D 3/00* | (2006.01) |
| *B01D 3/14* | (2006.01) |
| *C12M 1/00* | (2006.01) |

(52) U.S. Cl.
CPC ...... *B01D 11/0488* (2013.01); *B01D 11/0492* (2013.01); *C11B 1/10* (2013.01); *C11B 1/102* (2013.01); *C11B 1/108* (2013.01); *C11B 3/006* (2013.01); *C12M 43/00* (2013.01); *C12M 47/10* (2013.01); *C12P 7/06* (2013.01); *Y02E 50/17* (2013.01)

(58) Field of Classification Search
USPC ........................................................ 554/206
See application file for complete search history.

(56) References Cited

U.S. PATENT DOCUMENTS

| | | | |
|---|---|---|---|
| 3,878,232 | A | 4/1975 | Hayes et al. |
| 3,939,281 | A | 2/1976 | Schwengers |
| 4,174,315 | A | 11/1979 | Garrison et al. |
| 5,312,636 | A | 5/1994 | Myllymäki et al. |
| 5,460,814 | A | 10/1995 | Watanabe et al. |
| 5,602,286 | A | 2/1997 | Muralidhara |
| 5,843,499 | A | 12/1998 | Moreau et al. |
| 6,103,304 | A | 8/2000 | Mizuno |
| 6,166,231 | A | 12/2000 | Hoeksema |
| 6,201,142 | B1 | 3/2001 | Maza |
| 6,313,328 | B1 | 11/2001 | Ulrich et al. |
| 6,388,110 | B1 | 5/2002 | Ulrich et al. |
| 6,433,146 | B1 | 8/2002 | Cheryan |
| 6,610,867 | B2 | 8/2003 | Jakel et al. |
| 6,648,930 | B2 | 11/2003 | Ulrich et al. |
| 6,703,227 | B2 | 3/2004 | Jakel et al. |
| 6,723,370 | B2 | 4/2004 | Ulrich et al. |
| 6,740,508 | B2 | 5/2004 | Ulrich et al. |
| 6,927,048 | B2 | 8/2005 | Verser et al. |
| 2002/0113227 | A1 | 8/2002 | Kapila et al. |
| 2002/0183490 | A1 | 12/2002 | Cheryan |
| 2003/0077771 | A1 | 4/2003 | Verser et al. |
| 2003/0224496 | A1 | 12/2003 | Jakel et al. |
| 2004/0187863 | A1 | 9/2004 | Lanhauser |
| 2004/0234649 | A1 | 11/2004 | Lewis et al. |
| 2005/0049400 | A1 | 3/2005 | Cheryan |
| 2005/0220951 | A1 | 10/2005 | Abbas et al. |
| 2007/0099278 | A1 | 5/2007 | Aare |

FOREIGN PATENT DOCUMENTS

| | | | | |
|---|---|---|---|---|
| GB | 2 159 830 | | 12/1985 | |
| GB | 2159830 | A * | 12/1985 | .............. A23J 1/142 |
| WO | WO 2000/53791 | | 9/2000 | |
| WO | WO 2004/057255 | | 7/2004 | |
| WO | WO2004057255 | A * | 7/2004 | |
| WO | WO 2006/102685 | | 9/2006 | |

OTHER PUBLICATIONS

Cao et al., "Enzymatic Hydrolysis of Corn Starch After Extraction of Corn Oil with Ethanol", Applied Biochemistry and Biotechnology, vol. 57-58. pp. 39-47, Copyright 1996.
Database Medline [Online] US National Library of Medicine (NLM), Bethesda, MD, US: Oct. 2003 (Oct. 2003), National Toxicology Program: "NTP-CERHR Monograph on the Potential Human Reproductive and Developmental Effects of 1-Bromopropane (1-BP)." XP00238725 Database Accession No. NLM15995733 Abstract & NTP CHERHR MON. Oct. 2003, No. 9, Oct. 2003 (Oct. 2003), pp. i-III11, ISSN: 1556-2271.
Dien et al., "Review of Process for Producing Corn Fiber Oil and Ethanol from Quick Fiber", International Sugar Journal, vol. 107, No. 1275, pp. 186-191, Mar. 2005.
Dien et al., "Fermentation of "Quick Fiber" Produced from a Modified Corn-Milling Process into Ethanol and Recovery of Corn Fiber Oil", Applied Biochemistry and Biotechnology, vol. 113-116, pp. 937-9949, Copyright 2004.
Hojilla-Evangelista et al., "Sequential Extraction Processing of Flaked Whole Corn: Alternative Corn Fractionation Technology for Ethanol Production", American Association for Cereal Chemist, Inc., vols. 69(6), pp. 643-647, Copyright 1992.
Singh et al., "Recovery of Fiber in the Corn Dry-Grind Ethanol Process: A Feedstock for Valuable Coproducts", American Association for Cereal Chemist, Inc., vol. 76(6), pp. 868-872, Copyright 1999.
Taylor et al., "Fermentation and Cost of Fuel Ethanol from Corn with Quick-Germ Process", Applied Biochemistry and Biotechnology, vol. 94, pp. 41-49, Copyright 2001.
International Search Report and Written Opinion in International Application No. PCT/US2008/068805 dated Nov. 10, 2008.
Okafor, J.C. "Evaluation of Oils From Fermented and Unfermented Seeds of the African Oil Bean Tree Pentaclethra-Macrophylla," International Tree Crops Journal, vol. 7, No. 1-2, 1991, pp. 95-102.

\* cited by examiner

METHOD FOR EXTRACTING OIL FROM A WATER AND SOLIDS COMPOSITION, METHOD FOR THE PRODUCTION OF ETHANOL, AND ETHANOL PRODUCTION FACILITY

This application is a divisional application of U.S. application Ser. No. 14/011,342 that was filed with the United States Patent and Trademark Office on Aug. 27, 2013, which is a divisional application of U.S. application Ser. No. 12/215,913 that was filed with the United States Patent and Trademark Office on Jun. 30, 2008 and which granted as U.S. Pat. No. 8,518,673. This application claims priority to U.S. application Ser. No. 60/947,120 that was filed with the United States Patent and Trademark Office on Jun. 29, 2007. The entire disclosures of U.S. application Ser. Nos. 14/011,342, 12/215,913, and 60/947,120 are incorporated herein by reference.

FIELD OF THE DISCLOSURE

The present disclosure is directed to methods for extracting oil from a water and solids composition, to methods for the production of ethanol, and to an ethanol production facility.

BACKGROUND

Extraction of oil from edible items, such as grains (including corn), seeds, nuts, and legumes is common. Often, the item is ground, cracked, milled or otherwise processed to increase its surface area. Oil is then extracted from the ground item using various methods. Other materials are also commonly extracted from other vegetative materials.

One common method for extracting corn oil from corn is by using ethanol. Prior to contact with the ethanol, the corn kernels are crushed, flaked, milled, or otherwise modified into smaller pieces than the whole kernel. Because the majority of the oil is found in the germ of the kernel, the germ is often separated from the rest of the kernel. Ethanol is passed over, through, and otherwise around the corn pieces, and the oil leaches from the corn into the ethanol, where it is carried away from the remaining corn solids. The oil is then recovered from the ethanol. This process, however, can be costly, due to the high amounts of energy needed to separate the ethanol from the solids.

The recovery of oils from materials used in the fermentation process is desirable. Efforts have been made for the recovery of oils from seed germ prior to fermentation. For example, see Cao et al., *Enzymatic Hydrolysis of Corn Starch After Extraction of Corn Oil with Ethanol*, Applied Biochemistry and Biotechnology, Vol. 57/58, pages 39-47, 1996, and Hojilla-Evangelist et al., *Sequential Extraction Processing of Flaked Whole Corn: Alternative Corn Fractionation Technology for Ethanol Production*, Cereal Chemistry, 1992.

SUMMARY OF THE DISCLOSURE

A method for processing a water and solids composition for the recovery of oil is provided according to the present invention. The method include a step of extracting oil from a water and solids composition into an organic phase comprising an organic solvent to provide in the organic phase at least a portion of the oil. The water and solids composition refers to a composition containing alcohol, water, oil, and particulates. The oil can be associated with the solids, and the composition can be a result of a fermentation process. The water and solids composition can be referred to as a beer stream when it results from fermentation. Because the beer stream is a result of a fermentation process, it can be referred to as a fermentation broth even if it is no longer being subjected to fermentation. The beer stream can contain other components commonly found in a stream coming off a fermentation process such as, for example, glycerol, acetic acid, and yeast or other alcohol forming microorganism. In addition, the beer stream can include added material such as, for example, alcohol.

The alcohol in the water and solids composition (e.g., the beer stream) can assist with the separation of oil from the water and solids composition. One theory is that the alcohol interacts with the water in a manner that facilitates exposure or contact of the oil with the organic solvent thereby enhancing the ability of the organic solvent to pull the oil away from the solids. In order to assist with the extraction of the oil into the organic phase, the alcohol can be present in the water and solids composition in an amount of about 5 wt. % to about 30 wt. %, about 7 wt. % to about 20 wt. %, or about 10 wt. % to about 17 wt. %. A portion of the alcohol can be added, if desired, to increase the alcohol content to assist with extraction. For example, adding alcohol to provide a desired level of alcohol can increase the efficiency of the extraction process.

The water and solids composition can include oil that is desirable for recovery. In the case of production of a beer stream, various materials can be subjected to fermentation that include oil as a component desirable for recovery. Exemplary materials that can be fermented and that include oils desirable for recovery include grains and fruits. Exemplary grains include wheat, corn, and rice. Exemplary fruits include citrus fruits, and fermenting fruits. In addition, it may be desirable to recover oils that are added. For example, in the case of beer in the beverage industry, the oil that could be recovered may be present as a result of the hops or the yeast that has been added. Furthermore, materials that can be fermented include recycled materials that may contain oil. For example, candy products may be fermented, and may contain oils (e.g., aromatic oils such as spearmint) that may be desirable for recovery. The beer stream can contain a sufficient amount of oil to provide a desirable amount of oil recovered therefrom. For example, the beer stream can contain about 0.5 wt. % oil to about 2.5 wt. % oil. The step of extraction can provide for the recovery of at least about 75%, at least about 80%, at least about 90%, or at least about 95% of the oil present in the beer stream.

The organic solvent in the organic phase can be selected by balancing several characteristics desirable for the organic phase including, for example, the ability of the organic solvent to form a separate phase when mixed with beer stream (that is, the organic solvent is water immiscible), the ability of the organic solvent to pull the oil out of the beer stream in the presence of the alcohol, the low solubility of the organic solvent in alcohol, the relatively low evaporation temperature compared with the oil, and a low latent heat of vaporization. Examples of organic solvents suitable for extracting the oil from the beer stream include, for example, alkanes, alkenes, ethers, aromatic hydrocarbons, and mixtures thereof. The organic solvent can be provided as a halogenated organic solvent. A preferred organic solvent is hexane.

A method for producing ethanol is provided according to the present invention. The method includes steps of: fermenting a feed source comprising sugar and oil to form a fermentation broth comprising alcohol water, oil, and particulates; extracting oil from the fermentation broth into an organic solvent phase comprising an organic solvent to provide in the organic solvent phase at least a portion of the oil and forming a deoiled fermentation broth; and separating alcohol from the deoiled fermentation broth by distillation.

An ethanol production facility is provided according to the present invention. The ethanol production facility includes a source of fermentation broth, a liquid-liquid extractor, and a distillation system. The source of fermentation broth can be provided from one or more fermentors, and can be provided in a beer well. The fermentation broth can include oil, ethanol, water, and particulates. The liquid-liquid extractor is provided for the recovery of at least a portion of the oil from the fermentation broth, and includes an organic phase inlet, a fermentation broth inlet constructed to receive fermentation broth from the source of fermentation broth, a miscella outlet, and a deoiled fermentation broth outlet. The distillation system is constructed to receive deoiled fermentation broth from the liquid-liquid extractor and provide a volatile stream comprising concentrated ethanol.

DETAILED DESCRIPTION

Figure 1:
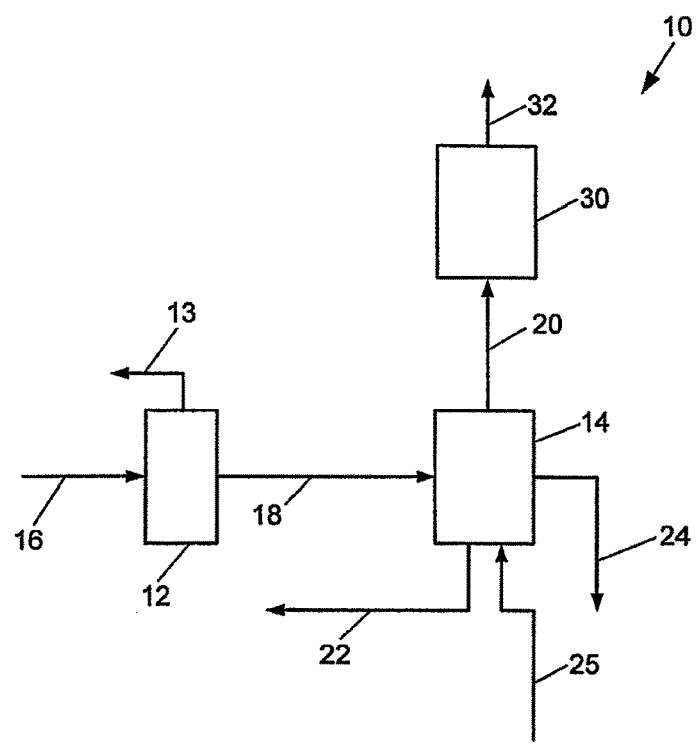
FIG. 1 is schematic diagram of a prior art process for the production ethanol.

In accordance with the present disclosure, oil can be recovered from materials containing the oil by extraction with an organic solvent and with alcohol. In the ethanol production industry, materials fermented to produce ethanol often contain oils that are valuable for recovery. An exemplary material commonly fermented to form ethanol is corn, and there is value in recovering corn oil. Other materials can be fermented to produce ethanol, and many of those materials also contain valuable oils that can be recovered. While it is desirable to recover oils from materials used in a fermentation process, it is recognized that oil can additionally be recovered from materials whether or not they were used in a fermentation process. For example, the presence of alcohol in combination with an organic solvent can be utilized to extract oil from a water and solids containing composition. The oil in the water and solids containing composition can contain oil associated in some manner with the solids (e.g., particulates) therein.

Oil can be extracted from a beer stream into an organic solvent to provide an organic phase containing the organic solvent and at least a portion of the oil from the beer stream. The beer stream refers to a composition containing alcohol (e.g., ethanol), water, oil, and particulates, and can be a result of a fermentation process. When the beer stream is a result of a fermentation process, it can be referred to as a fermentation broth even if it is no longer being subjected to fermentation. For example, the beer stream can be referred to as a fermentation broth even if alcohol and carbon dioxide are no longer being produced, and even if other components have been added to the fermentation broth. That is, there is no requirement that the beer stream or the fermentation broth are undergoing fermentation although it is likely, in many situations, that the beer stream or the fermentation broth are undergoing fermentation (although at a slow rate) when subjected to extraction for the removal of oil. In addition, it may be desirable in certain situations to add alcohol to the fermentation broth in order to enhance separation of the oil from the fermentation broth. The alcohol can be added to a beer stream containing alcohol in order to increase the amount of alcohol to a level that assists with oil extraction. The fermentation broth can still be referred to as a fermentation broth even though an additional component (e.g., alcohol) has been added or a component (e.g., oil) has been removed. After extraction, the fermentation broth can be referred to as the fermentation broth or as the deoiled fermentation broth. The fermentation broth, however, is no longer referred to as a fermentation broth after being subjected to distillation for the removal of alcohol. It should be understood that the water and solids composition is not limited to a fermentation broth. For example, the water and solids composition can be formed by adding alcohol to a composition containing water, oil, and particulates.

The organic phase containing extracted oil can be separated from the beer stream by known separation methods, such as decantation. The oil can then be separated from the organic solvent by known methods, such as by evaporation. The resulting beer stream, having reduced oil content, can then be returned to the ethanol production process at the point of removal. The beer stream can be sent to a distillation system for isolation of the ethanol. Any further processing can be accomplished by known methods, such as, for example, any of the various processes described in PCT Publication WO 2004/057255, which is incorporated herein by reference.

The beer can be provided as a result of various fermentation processes. Exemplary fermentation processes are described by, for example, U.S. Pat. No. 6,927,048 to Verser et al., U.S. Patent Publication No. U.S. 2004/0187863 to Langhauser, U.S. Patent Publication No. U.S. 2007/0099278 to Aare, and U.S. Patent Publication No. U.S. 2003/0077771 to Verser. The disclosure of these references are incorporated herein by reference.

Now referring to FIG. 1, a process for the production of ethanol is shown schematically at reference number 10. The process can be characterized as either a dry mill process or as a wet mill process. The process 10 includes a beer well 12 and a distillation system 14. In general, the beer well 12 receives beer 16 from a fermentor or a plurality of fermentors. Commercial ethanol producing facilities typically provide a beer well as a reservoir for receiving beer from several fermentors where the fermentation process in the fermentors is timed so that the fermentors release the beer to the beer well at a desired time. Typically, the fermentors are timed to release the beer to the beer well at about the same time or in a sequential manner so that the downstream processing can be continuous. Because fermentation is typically a batch process, collecting the beer in the beer well 12 allows for the downstream processing of the beer to be provided in a relatively continuous manner. Although the downstream processing is described as continuous, it should be understood that the downstream processing can provided as a batch process. The beer well 12 can include a carbon dioxide relief stream 13 for the removal of carbon dioxide. It is fairly common for the beer well 12 to give off carbon dioxide even though the beer 16 has left the fermentors. The beer well 12 (or the fermentors) can be considered as providing a source of fermentation broth.

The distillation system 14 is shown diagrammatically and can be provided, for example, in a commercial ethanol producing facility as a single distillation column or as a series of distillation columns arranged in parallel or in series. The energy for driving the distillation process can be provided in a number of ways. For the distillation system 14, water vapor 25 (e.g., steam) can be feed to the distillation system.

In general, the beer 18 flows from the beer well 12 to the distillation system 14 where the beer 18 is separated into a volatile fraction 20, a bottoms fraction 22, and an intermediate fraction 24. In general, the volatile fraction 20 includes alcohol and water, the bottoms fraction 22 includes stillage, and the intermediate fraction 24 includes water. The various fractions are not necessarily pure. For example, there may be alcohol and water in both the intermediate fraction 24 and the bottoms fraction 22.

The volatile fraction 20 generally includes alcohol and water. Because alcohol and water form an azeotrope, a separation process other than distillation can be provided to separate the remaining amount of water from the alcohol when it is desirable to provide a more pure alcohol. The volatile fraction 20 can be processed through a screening process 30 for the separation of alcohol and water. The screening process 30 can be referred to as a sieve. In order to separate an azeotropic mixture of alcohol and water, a technique other than distillation can be used such as the screening process 30 which is known in the art. The resulting purified alcohol 32 can be recovered. In general, the purified alcohol 32 can be provided as 100 wt. % alcohol. Typically, the level of alcohol in the volatile fraction 20 can be up to about 95 wt. % alcohol.

The bottoms fraction 22 can include stillage. In general, stillage includes a concentration of the particulates in the beer stream 18. In addition to the particulates, the stillage can include water, alcohol, oil, and other components such as glycerol and acetic acid, yeast, or other alcohol producing microorganism. The stillage can often be referred as whole stillage, and can be centrifuged for separation into at least two streams. One stream can include the relatively light components such as, for example, water, glycerol, and acetic acid, and can be treated and either discarded or recycled. The other stream can be referred as a high biological oxygen demand material and typically includes the particulates and the oil. The oil typically remains tied up with the particulates. The high biological oxygen demand material can be processed and recovered or disposed. Because of the presence of the oil in the material, the shelf life of the material can be relatively short. It is often desirable to use the material as livestock feed. The presence of the oil in the material, however, can cause the material to spoil.

Figure 2:
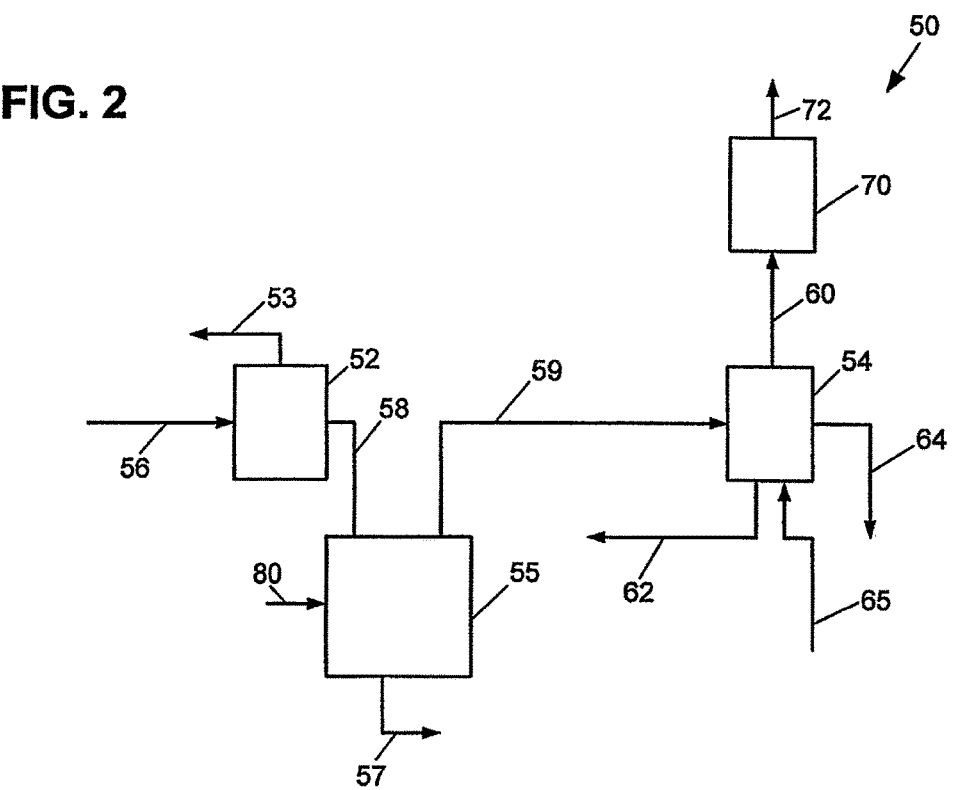
FIG. 2 is a schematic diagram of a process for producing ethanol according to the principles of the present invention.

Now referring to FIG. 2, a process for the production of ethanol, with the removal of oil, is shown at reference number 50. The process 50 includes a beer well 52, a distillation system 54, and an oil extractor 55. As discussed previously, the beer well 52 receives beer 56 from a fermentor or a plurality of fermentors. The fermentation process in the fermentors can be timed so that the fermentors release the beer to the beer well at a desired time. For example, the release can be staggered. Collecting the beer in the beer well 52 allows for the downstream processing of the beer to be provided in a relatively continuous manner. Alternatively, the downstream processing can be provided as batch, if desired. The beer well 52 can include a carbon dioxide relief stream 53 for the removal of carbon dioxide. The beer well 52 or the fermentors can be considered as providing a source of beer or fermentation broth.

The distillation system 54 is shown diagrammatically and can be provided, for example, as a single distillation column or as a series of distillation columns arranged in parallel or in series. The energy for driving the distillation system 54 can be provided by introducing water vapor 65 to the distillation system 65. Preferably, the water vapor 65 is provided as steam. Alternative ways of driving the distillation system are known, and can be utilized, if desired.

The beer 58 flows from the beer well 52 to the oil extractor 55 for the recovery of oil 57 and deoiled beer 59. The distillation system 54 is where the deoiled beer 59 is separated into a volatile fraction 60, a bottoms fraction 62, and an intermediate fraction 64. In general, the volatile fraction 60 includes alcohol and water, the bottoms fraction 62 includes stillage, and the intermediate fraction 64 includes water. The various fractions are not necessarily pure. For example, there may be alcohol and water in both the intermediate fraction 64 and the bottoms fraction 62. The volatile fraction 60 generally includes alcohol and water. Because alcohol and water form an azeotrope, a separation process can be utilize to separate the remaining amount of water from the alcohol when it is desirable to provide additional separation. The volatile fraction 60 can be processed through a screening process 70 for the separation of alcohol and water. The screening process 70 can be referred to as a sieve. In order to separate an azeotropic mixture of alcohol and water, a technique other than distillation can be used such as the screening process 70. The resulting purified alcohol 72 can be recovered. In general, the purified alcohol 72 can be provided up to about 100 wt. % alcohol. Typically, the level of alcohol in the volatile fraction 60 can be up to about 95 wt. % alcohol.

The bottoms fraction 62 can include stillage. In general, stillage includes a concentration of the particulates from the deoiled beer stream 59. The stillage can be referred to deoiled stillage, and can be centrifuged for separation into at least two streams. One stream can be referred to as a relatively light stream and includes the relatively light components such as, for example, water, alcohol, and other components that might be present including glycerol and acetic acid. The other component can be referred to as a relatively heavy stream and can include the heavier components such as the particulates. It should be understood, however, that the relatively heavy stream can also include water and alcohol. Because of the removal of oil in the oil extractor 55, there is a reduced amount of oil present in the stillage. Because of a reduced amount of oil, the shelf life of the stillage can be enhanced, and the stillage may be more useful as an animal feed source compared with stillage that contains a larger amount of oil.

The oil extractor 55 can be characterized as either a liquid-liquid extractor or a liquid-solid extractor. In general, the oil present in the beer stream 58 is typically associated with the particulates in the beer stream 58. The extent of the association of the oil with the particulates is not fully understood. Because the oil is not very soluble in water, one theory is that the oil becomes more associated with the particulates in a water based stream containing the oil and particulates. The particulates can be referred to as fermentation particulates or stillage forming particulates. The beer stream 58 can typically be considered a liquid even though there are particulates within the liquid. By introducing an organic phase 80 to the oil extractor 55, it is possible to extract oil from the beer stream 58 into the organic phase 80 to provide an organic phase containing at least a portion of the oil. While it may be desirable to extract all of the oil from the beer stream 58, the level of oil recovery can be at least about 75%. As a result of the separation of oil from the beer stream 58, it is recognized that the deoiled beer stream 59 may contain oil although at a reduced concentration compared with the beer stream 58. It is generally desirable to recover as much of the oil as possible from the beer stream 58. Accordingly, it is desirable to recover at least about 75% of the oil from the beer stream 58. In addition, as a result of extraction, the deoiled beer stream 59 may contain a greater weight percent of alcohol.

Figure 3:
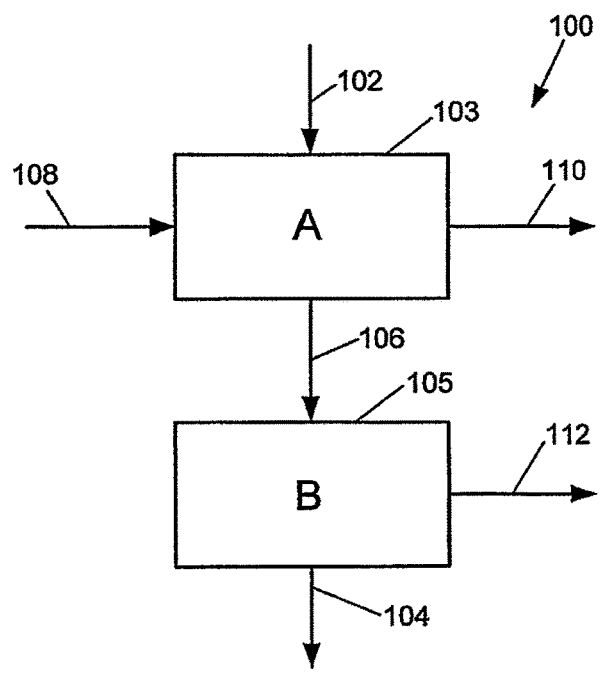
FIG. 3 is a generic flow diagram showing oil extraction from a beer stream according to the principles of the present invention.

An oil extraction process can be characterized by the generic flow diagram shown in FIG. 3 at reference number 100. The oil extraction process 100 includes two subprocesses. The subprocesses include process A which is the extraction of oil from a beer stream 102, and process B which is a separation of oil 104 from an organic phase containing oil 106.

In process A, the beer stream 102 is combined with an organic solvent 108 in the extractor 103. The beer stream 102 and the organic solvent 108 can be allowed to contact each other for a sufficient amount of time to allow for oil to move from the beer stream 102 to the organic solvent 108. The total residence time in the oil extractor 103 can vary. An exemplary residence time that can provide desired removal of the oil is about 10 minutes to about 40 minutes. In addition, the ratio of the beer stream 102 to the organic solvent 108 can be selected to provide the desired separation of the oil from the beer stream 102 while also considering the subsequent desirability of separating the oil from the organic solvent. For example, increasing the amount of organic solvent in the oil extractor 103 can help increase the level a separation of the oil from the beer stream 102. At some point, however, the increase separation of oil from the beer stream 102 may be negated by the added cost necessary to separate the oil from the organic solvent. An exemplary volumetric ratio of the beer stream to the organic solvent can be about 1:3 to about 3:1, and preferably about 2:1 to about 1:2. A desired volumetric ratio of the beer stream to the organic solvent can be about 1:1.

The organic solvent is selected so that it provides a separation phase when combined with the beer stream, and allows for the separation of oil from the beer stream. In addition, the organic solvent can be selected to provide easy of separation of the oil from the organic solvent. The solvent can be select to provide relatively low solubility with ethanol, low solubility with water, and ease of separation from the oil generally based on differential heat of vaporization or enthalpy of vaporization.

The type and amount of organic solvent can be selected to provide a desired level of separation of the oil from the beer stream. In general, it is expected that not all of the oil will be separated from the beer stream. That is, less than 100% of the oil will likely be removed from the beer stream by extraction. Preferably, at least about 75% of the oil can be removed from the beer stream by extraction. Preferably, at least about 80%, at least about 90%, or at least about 95% of the oil in the beer stream can be recovered by extraction.

As a result of extraction in the oil extractor 103, the solvent phase containing oil 106 is recovered and the deoiled beer stream 110 is recovered. The organic phase containing oil 106 can be referred to as miscella. The deoiled beer steam 110 comprises the beer steam 102 minus the oil, and can be referred to as the spent beer stream or the spent fermentation broth.

Exemplary organic solvents that can be used include alkanes, alkenes, ethers, aldehydes, aromatic hydrocarbons, and mixtures thereof. In addition, the organic solvents can be halogenated form of the organic solvents. An exemplary alkane that can be used includes hexane. An exemplary halogenated solvent that can be used includes n-propyl bromide.

In process B, the miscella 106 is treated for the separation of the oil 104 from the organic phase 112 in the evaporator 105. The oil 104 can be referred to crude oil, and is typically recovered as a result of heating and boiling off the organic phase. The resulting organic phase 112 can be reclaimed and reused. The evaporator 105 can be provided as a falling film or other type of evaporator. The separation may be done at atmospheric conditions or under a vacuum.

In a dry mill, fuels ethanol plant, the beer stream to the liquid liquid extractor can contain, for example, about 13 wt. % ethanol, about 2 wt. % glycerin, about 2 wt. % oil, about 12 wt. % solids, and about 71 wt. % water. Approximately 88% of the oil present in the beer stream is understood to be contained within the solids, and the remainder is understood to be residing closely with the solids.

As mentioned above, the presence of the ethanol in the feed stream allows the solvent to extract the oil out of the solids. The ethanol acts to bind the water present, which in turn allows the solvent to contact the solids and the oil. Generally, the feed stream contains sufficient levels of ethanol to enable this process. However, ethanol can be added to the feed stream if there is an insufficient pre-existing amount of a water binding agent. In addition, other alcohols may be useful in the extraction process. Exemplary alcohols that can be used with ethanol or in place of ethanol include short chain alcohols such as, for example, alcohols containing six or fewer carbon atoms. Exemplary short chain alcohols include ethanol, propanol, isopropanol, butanol, pentanol, hexanol, and mixtures thereof. Furthermore, the short chain alcohol(s) can be added to assist with the extraction.

As an example, from an initial corn feed of 700 lb/min (which has about 14 lbs oil), approximately 11 lbs of crude corn oil can be readily obtained. The amount of oil obtained is dependent on the extraction efficiency, but typically the amount of oil obtained will be at least 75%, often at least 80%, preferably at least 90%, and most preferably at least 95% of the total oil present in the initial corn feed. The oil not removed via the extraction remains in the beer stream with the corn solids.

Figure 4:
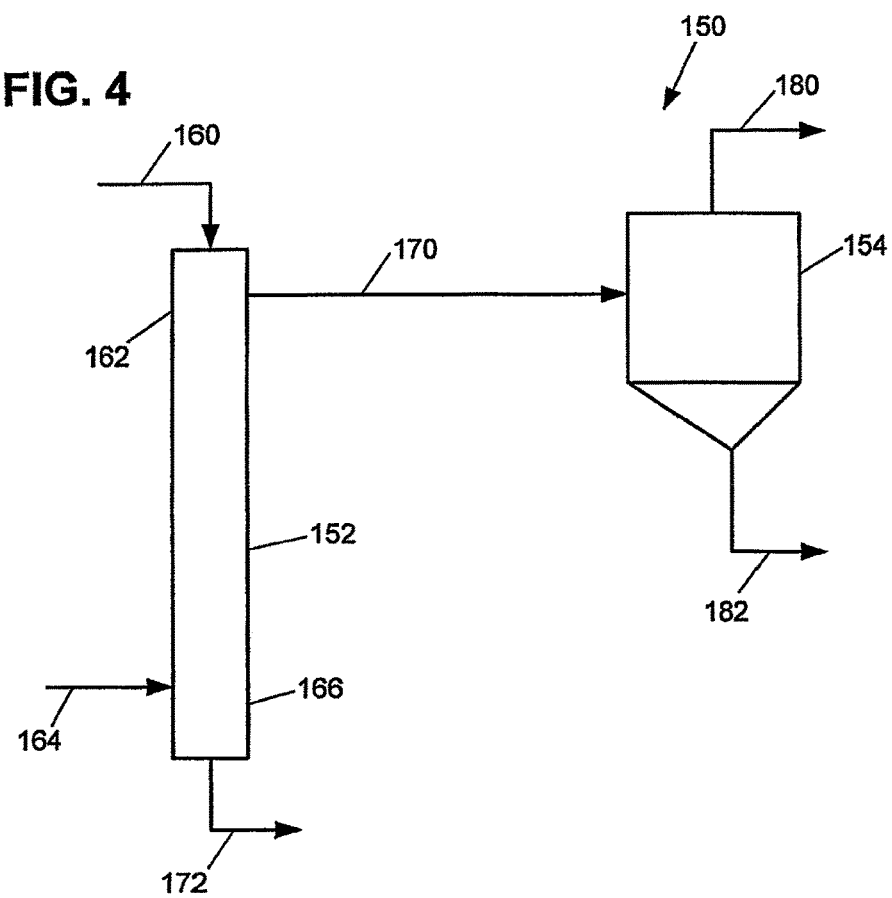
FIG. 4 is a schematic diagram of an exemplary oil extraction method according to the principles of present invention.

Now referring to FIG. 4, an apparatus for the extraction and recovery of oil is shown at reference number 150. The apparatus 150 includes a liquid liquid extraction column 152, and an evaporator 154. In general, beer 160 enters the liquid-liquid extraction column 152 near the top 162, and an organic solvent 164 enters the column 152 near the bottom 166. For this liquid-liquid extraction column, the beer stream 160 is heavier than the organic solvent 164 and, as a result, the organic solvent 164 flows toward the upper part 162 and the beer stream 160 flows toward the bottom 166. As a result of residence and contact within the column 152, the oil moves from the beer stream 160 to the organic phase generated by the organic solvent 164. The resulting miscella 170 (containing organic solvent and oil) leaves the column 152 and is processed to the evaporator 154. The deoiled beer 172 can be referred to spent beer and can be processed for the recovery of alcohol by, for example, distillation. In the evaporator 154, the miscella 170 is processed for the separation of the oil and the organic solvent. Typically, the separation is caused by heating the miscella so that the organic solvent is evaporated. The organic solvent can be recovered via the organic solvent outlet 180, and the oil can be recovered via the oil outlet 182. The oil recovered via the outlet can be referred to as concentrated or cure oil.

For the apparatus in FIG. 4, the beer stream can be provided as a fermentation broth resulting from the fermentation of corn, and the organic solvent provided can be hexane. Furthermore, the volumetric ratio of the beer stream to hexane can be about 3:1 to about 1:3, and can be about 2:1 to about 1:2. As the column 152 fills from the top with the beer stream and from the bottom with hexane, two layers form. As the hexane rises up through the beer stream, the hexane and the beer stream contact and at least a portion of the oil dissolves in the hexane. The resulting miscella can be conveyed to the evaporator where the stream is heated to a temperature and pressure such that it causes the hexane to vaporize and separate from the oil. The hexane can be conveyed to a low temperature source such as a condenser where the vapors are cooled to the point of becoming a liquid again. Once a liquid, the hexane can be discarded or sent to storage for recycle/reuse in the extraction process or in another process.

As the hexane is vaporized and removed from the miscella, the oil becomes more concentrated. The concentrated (or crude) oil is sent to storage or is further processed for additional removal of hexane or other impurities.

The evaporator may be run at atmospheric pressure or at a reduced pressure. The evaporator may be of several design types or may be in several stages. The extractor may also be of several design configurations from something as simple as an empty column to one full of stages and agitators.

While the process has been exemplified in the context of recovery of corn oil, it should be understood that the process can be applied to other vegetable oils and to non-vegetable oils such as oils found in a fermentation broth or non-fermentation broth. Exemplary non-vegetable oils that can be recovered from a fermentation broth include those oils from fruit (e.g., citrus fruit and fermenting fruits), from hops, from yeast, from additives to reduce foaming, from a recycle material (e.g., candy), etc. In general, the reference to a water and solids composition refers to a composition that contains water (preferably at least about 50 wt. % water), solids (e.g., particulates), oil associated with the solids, and a sufficient amount of alcohol to assist with the extraction into an organic phase. The particulates can be provided as a result of grinding or pulverizing a material to increase surface area, and can be provided to include yeast. The water and solids composition can be provided as a beer stream or as a fermentation broth, or it can be a composition that has not been subjected to fermentation.

The foregoing description, which has been disclosed by way of the above discussion and the drawings, addresses embodiments of the present disclosure encompassing the principles of the present invention. The methods maybe changed, modified and/or implemented using various types of equipment and arrangements. Those skilled in the art will readily recognize various modifications and changes which may be made to the described methods and equipment without strictly following the exemplary embodiments illustrated and described herein, and without departing from the scope of the present invention.

What is claimed:

1. A method for extracting oil from an extraction composition, the method comprising steps of:
   (a) adding alcohol to a water and solids composition to form an extraction composition that has not been subject to fermentation, the extraction composition comprising water, solids, oil associated with the solids, and a sufficient amount of alcohol to assist with the extraction of the oil from the composition, wherein the water and solids composition contains at least 50 wt. % water;
   (b) extracting the oil from the extraction composition of step (a) with an organic solvent selected from the group consisting of alkanes, alkenes, ethers, aldehydes, aromatic hydrocarbons, and mixtures thereof and forming:
      (i) a miscella comprising the organic solvent and the oil; and
      (ii) a deoiled water and solids composition comprising the water, the solids, and the alcohol; and
   (c) separating the oil from the organic solvent in the miscella.

2. A method for extracting oil from an extraction composition according to claim 1, wherein the organic solvent comprises a halogenated organic solvent.

3. A method for extracting oil from an extraction composition according to claim 1, wherein the step of extracting comprises combining the extraction composition with the organic solvent at a weight ratio of the extraction composition to the organic solvent of about 3:1 to about 1:3.

4. A method for extracting oil from an extraction composition according to claim 1, wherein the step of extracting comprising combining the extraction composition with the organic solvent at a weight ration of the extraction composition to the organic solvent of about 2:1 to 1:2.

5. A method for extracting oil from an extraction composition according to claim 1, wherein the extraction composition comprises alcohol, oil, water, and particulates.

6. A method for extracting oil from an extraction composition according to claim 1, wherein the extraction composition comprises about 5 wt. % to about 30 wt. % ethanol.

7. A method for extracting oil from an extraction composition according to claim 1, wherein the extraction composition comprises about 0.5 wt. % to about 2.5 wt. % oil.

8. A method for extracting oil from an extraction composition according to claim 1, wherein at least about 75% of the oil in the extraction composition is extracted.

* * * * *